United States Patent [19]

Finkenberg

[11] Patent Number: 4,989,613
[45] Date of Patent: Feb. 5, 1991

[54] DIAGNOSIS BY INTRASOUND

[76] Inventor: John G. Finkenberg, 1322 S. Gertruda, Redondo Beach, Calif. 90277

[21] Appl. No.: 415,096

[22] Filed: Sep. 29, 1989

[51] Int. Cl.$^5$ .............................................. A61B 8/00
[52] U.S. Cl. ..................................... 128/739; 128/32; 128/77
[58] Field of Search ...................... 128/739, 32, 36, 41, 128/64, 67, 77, 661.03, 660.06, 630; 73/570, 574, 579, 588

[56] References Cited

U.S. PATENT DOCUMENTS

| | | | |
|---|---|---|---|
| 3,477,422 | 11/1969 | Jurist et al. | 128/630 |
| 3,779,238 | 12/1973 | Cutler et al. | 128/36 |
| 4,048,986 | 9/1977 | Ott | 128/660.01 |
| 4,217,912 | 8/1980 | Hubmann et al. | 73/574 |
| 4,361,154 | 11/1982 | Pratt, Jr. | 128/660.01 |
| 4,632,095 | 12/1986 | Libin | 128/67 |

OTHER PUBLICATIONS

Illustrated Stedman's Medical Dictionary, 24th Edition, Copyright by Williams & Wilkins, 1982, p. 1209.
DeGowin et al., Bedside Diagnostic Examination 2nd Edition, Copywright by MacMillan Company, 1969, pp. 612-613 and 644.

Primary Examiner—Kyle L. Howell
Assistant Examiner—Krista M. Pfaffle
Attorney, Agent, or Firm—Fulwider, Patton, Lee & Utecht

[57] ABSTRACT

A non-invasive, non-irradiating, simple and inexpensive method of confirming suspected bone fractures wherein intrasonic vibration is induced in and about the bone near the typically inflamed area. A protective retraction response is elicited in substantially all cases where a fracture is in fact present while a false positive is only rarely observed.

6 Claims, 1 Drawing Sheet

DIAGNOSIS BY INTRASOUND

BACKGROUND OF THE INVENTION

1. Field of the Invention

This invention relates to orthopedic diagnostic techniques and more particularly pertains to a non-invasive, non-irradiating method of confirming suspected bone fractures.

2. Brief Description of the Prior Art

Bone fractures are most often diagnosed or confirmed radiographically. Certain fractures in certain bones are, however, hard to detect via an X-ray series and may require additional, costly and time consuming procedures to confirm. Often such procedures call for further exposure to radiation which is, of course, preferably avoided or minimized.

A fracture of the carpal scaphoid may be particularly hard to detect and is susceptible to misdiagnosis. The unique distal to proximal blood supply of the carpal scaphoid and the major shear stresses imposed upon it by its linkage role in carpal kinematics predispose scaphoid fractures to complications. Fracture nonunions of the scaphoid may result in a post-traumatic arthritis many years after the injury which is disabling due to the scaphoid's articulation with the distal radius and four of the seven carpal bones. It is therefore extremely important that such a fracture be promptly and correctly diagnosed to ensure proper treatment.

Presently, post-trauma patients with tenderness in the anatomic snuffbox between the extensor pollicus longus and extensor pollicus brevis are placed in thumb spica casts despite negative plain film X-rays The patient is asked to return in ten to fourteen days for repeat X-rays and an examination out of plaster. If there is a negative clinical exam and normal X-rays the injury is treated as a resolving wrist sprain. If a fracture is not noted on the delayed X-rays and the patient continues to have tenderness in the anatomic "snuffbox", the patient is immobilized in another thumb spica cast.

Technetium bone scans have been advocated for the early diagnosis of scaphoid fractures to avoid the 2-3 week delay required by conventional techniques. Such bones scans have been reported to be 100% sensitive in the diagnosis of scaphoid fractures at 72 hours. In an effort to decrease costs and radiation exposures it has been concluded that scans should be performed after 10-14 days if the patient was clinically positive and radiographically negative. This was found to spare approximately 70% of the patients from requiring a bone scan. The radiation dose to the patient's hands is minimal although the bladder receives 2.5-5 Rads.

Bone scans have been described as 100% sensitive and 75% specific in detecting scaphoid fractures. False positives include arthrosis, tenosynovitis, cysts, unfused epiphysis scapholunate dislocations and Kienbock's disease. In addition, the trapezoid/trapezium region has demonstrated a disproportionate amount of positive increased uptake results with no fractures revealed on delayed X-rays.

In light of these shortcomings, an improved method of diagnosing occult fractures such as fractures of the carpal scaphoid is therefore called for that provides a fast, simple, reliable and inexpensive means of confirming suspected fractures.

SUMMARY OF THE INVENTION

The present invention provides a diagnostic technique whereby intrasonic vibration is induced in and around a bone which is suspected of being fractured. A fracture is positively indicated if such vibration causes sufficient discomfort to produce a protective retraction response by the patient.

In the case of a suspected scaphoid fracture, the technique calls for the application of a vibrating element directly to the surface of the inflamed region of the wrist. Gradually increasing the intensity of the vibration which nominally consists of a mixture of frequencies between 200–12,000 Hz, to a maximum of about 100 milliwatts is effective to elicit a positive response in virtually all scaphoid fractures. A false positive response is only rarely observed. The discomfort associated with a positive response is immediately alleviated upon removal of the vibrating element.

A variety of vibrating element or head configurations can be employed to transmit vibrations from an electrically driven vibrator to the body. A head configuration shaped to maximize the transfer of vibration to the particular body region where a fracture is suspected has been found to be especially effective. A head substantially conforming to a section of the wrist, for example, can be used to confirm scaphoid fractures.

Other features and advantages of the invention will become apparent from the following detailed description, taken in conjunction with the accompanying drawings which illustrate, by way of example, the features of the invention.

DETAILED DESCRIPTION OF THE INVENTION

Figure 1:
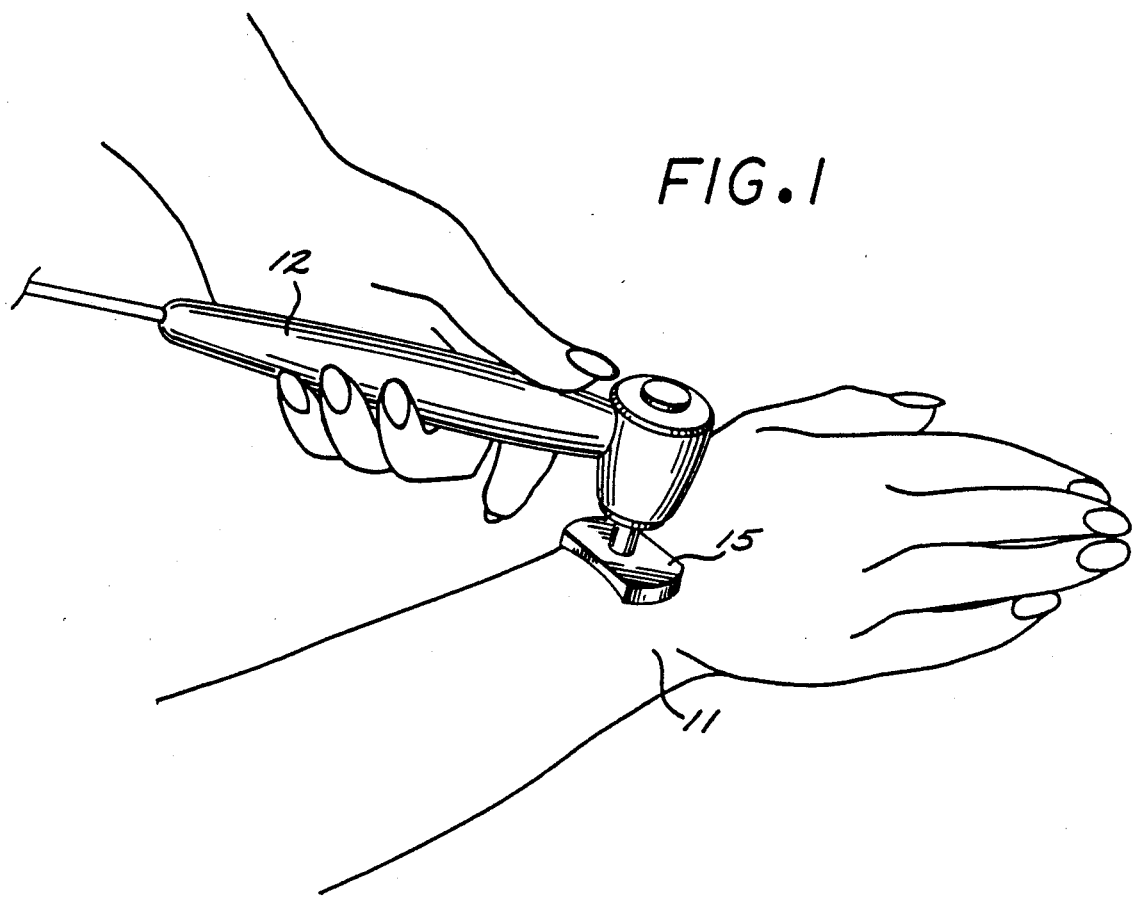
FIG. 1 illustrates the method of the present invention being applied to a patient's wrist.

The present invention provides a method for confirming suspected bone fractures and is especially useful when such fractures cannot readily be detected by an X-ray series, such as is often the case in carpal scaphoid fractures. The present invention provides a reliable, fast, safe and inexpensive method wherein an element 15 vibrating in the intrasonic frequency range is applied directly against the inflamed region 11 above a suspected fracture as illustrated in FIG. 1.

Intrasound is defined as those audible frequencies that lie between 20 and 20,000 Hz. Infrasound (below 20 Hz) and ultrasound (above 20,000 Hz) are not audible.

Fracture of the carpal scaphoid is the most common fracture of the carpus and the most commonly undiagnosed fracture of the upper extremity. When diagnosed, acute stable fractures are expected to have a 90–95% union rate if placed in a thumb spica cast for approximately 10 weeks. Fractures that remain displaced or unstable are usually treated by open reduction and internal fixation since closed management results in bone union in only 54%. A delay in the diagnosis of this fracture decreases the chances for uncomplicated bone union. Up to 40% of fracture nonunions of the scaphoid are undiagnosed at the time of the original injury.

The blood supply to the scaphoid is from the dorsal branch of the radial artery. It enters the bone distally from the lateral-volar as well as the dorsal aspects and extends proximally. This unique blood supply may predispose the scaphoid to nonunion since approximately one third of the proximal scaphoid fractures result in a vascular necrosis of the proximal fracture fragment Fracture nonunions of the scaphoid frequently result in disabling post-traumatic arthritis many years after the injury.

For the purposes of diagnosing or for confirming what is suspected to be a fracture of the carpal scaphoid, it has been found that inducing an intrasonic vibration, more specifically a mixture of frequencies between 200–12,000 Hz, within and around the carpal scaphoid elicits a protective retraction response in substantially only those patients that actually have suffered a fracture therein.

Figure 2:
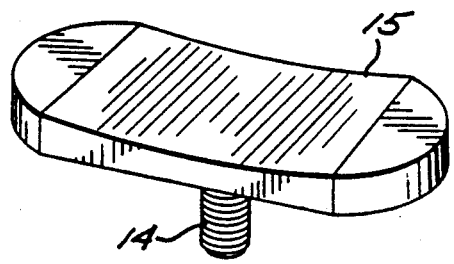
FIG. 2 illustrates an enlarged perspective of the vibrator head employed in FIG. 1.

The device employed to induce such vibration consists of an electrically driven vibrator 12 fitted with a shaped head with which the region proximate to the suspected fracture can best be accessed. FIG. 2 illustrates such a head configuration especially well adapted for application to the wrists. The generally arcuate flat surface 15 is removably attachable to the vibrator 12 by a threaded stud 14. Alternatively, a conical head configuration 16 can be used when a more concentrated point of transfer is desired.

It has been found that by gradually increasing the intensity of vibration to a maximum, which in the case of scaphoid fractures is about 100 milliwatts, a point is reached where the positive response is elicited in case of actual fracture.

Other fractures in different bones and at different locations will respond to different frequencies and to different intensities. A provision for varying the vibrating frequency of the vibrating element allows the diagnostic technique of the present invention to be performed on a variety of different fracture sites.

EXAMPLE

Figure 3:
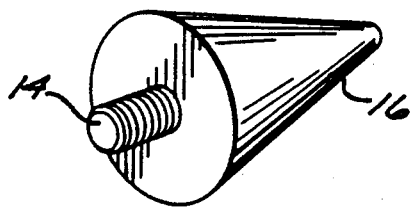
FIG. 3 illustrates an alternative vibrator head configuration useful for confirming occult bone fractures.

Fifty patients with a clinical diagnosis of occult scaphoid fracture participated in a study in which the efficacy of the method of the present invention was tested. The device used to induce vibration is commercially available from ORTHOSONIC and requires a 110–120 volts AC, 60 cycle power source. An output of variable intensity up to a maximum of 100 milliwatts provides a mixture of frequencies between 200 and 12,000 Hz. The head configuration used for this particular study was the substantially conical shape illustrated in FIG. 3.

To reduce physician bias, the results of clinical examination and scaphoid X-rays were unknown to the physicians performing the test. Occult scaphoid fractures were defined as post-traumatic, radiographically negative wrist injuries in patients presenting with anatomic "snuffbox" tenderness. The vibrating head element was placed on the snuffbox region, radial styloid, proximal and distal scaphoid poles. The test was begun at the lowest intensity and gradually increased to the highest intensity over approximately 15 seconds. The subjective quantitation of pain was recorded from each patient throughout testing. A similar testing sequence was recorded on the uninjured wrist which served as a control. A positive intrasound exam was defined as eliciting enough discomfort to produce a protective retraction response by the patient.

A limited two-phase technetium bone scan was obtained on every patient who demonstrated snuffbox tenderness and radiographically negative X-rays 10–14 days post-trauma. Static images of the bilateral wrists were obtained in the gamma camera equipped with a low energy, high resolution parallel hole collimator to 300K counts at ten minutes and at three hours after IV administration of 925 MBg (25 mCi) of technetium 99m methylene diphosphonate. Initial blood flow images were graded as positive or negative for hyperemia to aid in separating out chronic changes. Static images were reviewed by a radiologist for focal or generalized increased uptake. Radiographic correlation was used to assist in excluding degenerative changes as this often results in increased uptake on the bone scan. Scaphoid X-rays were taken on every patient at the initial, two week and subsequent visits.

All patients with snuffbox tenderness were placed in a short-arm thumb spica cast despite findings on the vibratory examination. The cast was removed prior to the bone scan, at each clinic visit and when it was determined that the patient did not have a scaphoid fracture. Scaphoid fractures, when discovered radiographically, were treated with conservative techniques.

Follow-up clinical examination revealed no snuffbox tenderness in 14/50 patients. All of these patients had a negative vibratory exam on initial presentation. The remaining patients had a limited two-phase bone scan which demonstrated increased uptake in the wrist on 14/36 patients (38%). Eight of these patients had a positive vibratory exam and the remaining 28 patients tested negative. The location of the increased uptake was distributed between the scaphoid (6), distal radius (4) and carpals (4) diffusely. Delayed scaphoid view X-rays demonstrated six scaphoid fractures. The vibratory testing was positive on all six of these patients when placed over the snuffbox and scaphoid poles (sensitivity 100%). The apparatus gave a false positive response in two patients: one had a trapezium fracture and another had reflex sympathetic dystrophy (specificity 96%). In this particular study, the apparatus was found to have a positive predictive value of 75% (6/8), negative predictive value of 100% (42/42) and to be 96% (48/50) accurate.

While a particular form of the invention has been illustrated and described, it will also be apparent to those skilled in the art that various modifications can be made without departing from the spirit and scope of the invention. Accordingly, it is not intended that the invention be limited except as by the appended claims.

What is claimed is:

1. A method of confirming a suspected occult fracture of a patient's bone, comprising the steps of:
   inducing intrasonic vibration in said bone; and
   observing a protective retraction response by said patient to said induced vibration as an indication of said occult fracture.

2. The method of claim 1 wherein said vibration is induced in said bone by applying a vibrating element to the patient in a region proximate to the suspected fracture.

3. The method of claim 2 wherein the method is employed to confirm a suspected fracture of the carpal scaphoid, comprising the step of applying said vibrating element to a patient's wrist and said intrasonic vibration comprises a mixture of frequencies between 200 and 12,000 Hz.

4. The method of claim 3 wherein said vibration is gradually increased to a maximum intensity of 100 milliwatts.

5. The method of claim 1 wherein said vibration has an intensity and wherein said method further comprises a step of gradually increasing the intensity of said vibration to a predefined maximum.

6. The method of claim 1 wherein said vibration has a frequency and wherein said method further comprises a step of varying the frequency of said vibration.

* * * * *